United States Patent
Ueno et al.

(10) Patent No.: US 7,465,944 B2
(45) Date of Patent: Dec. 16, 2008

(54) CHARGED PARTICLE THERAPY APPARATUS AND CHARGED PARTICLE THERAPY SYSTEM

(75) Inventors: Daisuke Ueno, Hitachi (JP); Daishun Chiba, Hitachi (JP); Yasutake Fujishima, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/405,648

(22) Filed: Apr. 18, 2006

(65) Prior Publication Data
US 2006/0219948 A1    Oct. 5, 2006

Related U.S. Application Data

(63) Continuation of application No. 10/884,971, filed on Jul. 7, 2004, now abandoned.

(30) Foreign Application Priority Data

Jul. 7, 2003    (JP)    ............... 2003-192535

(51) Int. Cl.
 G21G 1/00    (2006.01)
(52) U.S. Cl. .................... 250/492.3; 250/398
(58) Field of Classification Search ............. 250/492.3, 250/398, 492.1; 378/65; 600/1, 2
See application file for complete search history.

(56) References Cited

U.S. PATENT DOCUMENTS

| | | | |
|---|---|---|---|
| 4,870,287 A | | 9/1989 | Cole et al. |
| 5,260,581 A | | 11/1993 | Lesyna et al. |
| 5,538,494 A | * | 7/1996 | Matsuda ................... 600/1 |
| 5,585,642 A | | 12/1996 | Britton et al. |
| 5,698,954 A | * | 12/1997 | Hirota et al. ............ 315/503 |
| 5,895,926 A | | 4/1999 | Britton et al. |
| 6,683,318 B1 | | 1/2004 | Haberer et al. |
| 7,012,267 B2 | * | 3/2006 | Moriyama et al. ........ 250/492.3 |
| 7,173,264 B2 | * | 2/2007 | Moriyama et al. ........ 250/492.3 |
| 7,262,424 B2 | * | 8/2007 | Moriyama et al. ........ 250/492.3 |

FOREIGN PATENT DOCUMENTS

| | | |
|---|---|---|
| JP | 5-35154 | 5/1993 |
| JP | 5-223987 | 9/1993 |
| JP | 08-229145 | 9/1996 |
| JP | 11-501232 | 2/1999 |
| JP | 2001-137372 | 5/2001 |

* cited by examiner

Primary Examiner—Kiet T Nguyen
(74) Attorney, Agent, or Firm—Dickstein Shapiro LLP

(57) ABSTRACT

A charged particle therapy system is disclosed in which a hard switch for making a beam request of the accelerator side is installed in an irradiation room so that the accelerator side can start a desired beam irradiation preparation after depressing the hard switch. This arrangement allows the accelerator allocated time to be reduced, thereby improving the usage efficiency of the facilities by increasing the throughput with respect to patients.

8 Claims, 8 Drawing Sheets

401:HARD SWITCH FOR BEAM REQUEST

CHARGED PARTICLE THERAPY APPARATUS AND CHARGED PARTICLE THERAPY SYSTEM

This is a continuation of Application No. 10/884,971, filed on Jul. 7, 2004 now abandoned, the entire disclosure of which is incorporated herein by reference.

BACKGROUND OF THE INVENTION

The present invention relates to a charged particle therapy apparatus and a charged particle therapy system.

In the irradiation therapy using a medical accelerator, an operator performs positioning with respect to a patient in an irradiation room, and thereafter enters an irradiation operation room from the irradiation room through a passage. Then, the operator sends a desired beam request from a console provided in the irradiation operation room to the accelerator control side. The passage in the irradiation room has a labyrinth-like configuration in order to shield against radiation, and a protective door at the outlet of the irradiation room is constituted by a large-sized electric door because a large shielding work load. Such techniques are disclosed, for example, in JP, A 5-223987.

SUMMARY OF THE INVENTION

In the above-described related art, after having performed positioning with respect to a patient, an operator enters an irradiation operation room from the irradiation room through the labyrinth-like passage, then the operator requires beams to the accelerator side, and from that point in time, the accelerator side starts a preparation for required beams. The operator in the irradiation operation room, therefore, must wait for some time until the preparation for beam transport is made.

The object of the present invention is to allow the accelerator to be efficiently used, and enable the throughput with respect to patients to be enhanced by reducing the accelerator allocation time.

To solve the above-described object, the present invention provides a medical accelerator control system in which a hard switch for beam request is arranged in an irradiation room. This arrangement allows the accelerator side to start a desired beam irradiation preparation after depressing the hard switch.

DETAILED DESCRIPTION OF THE PREFERRED EMBODIMENTS

Figure 1:
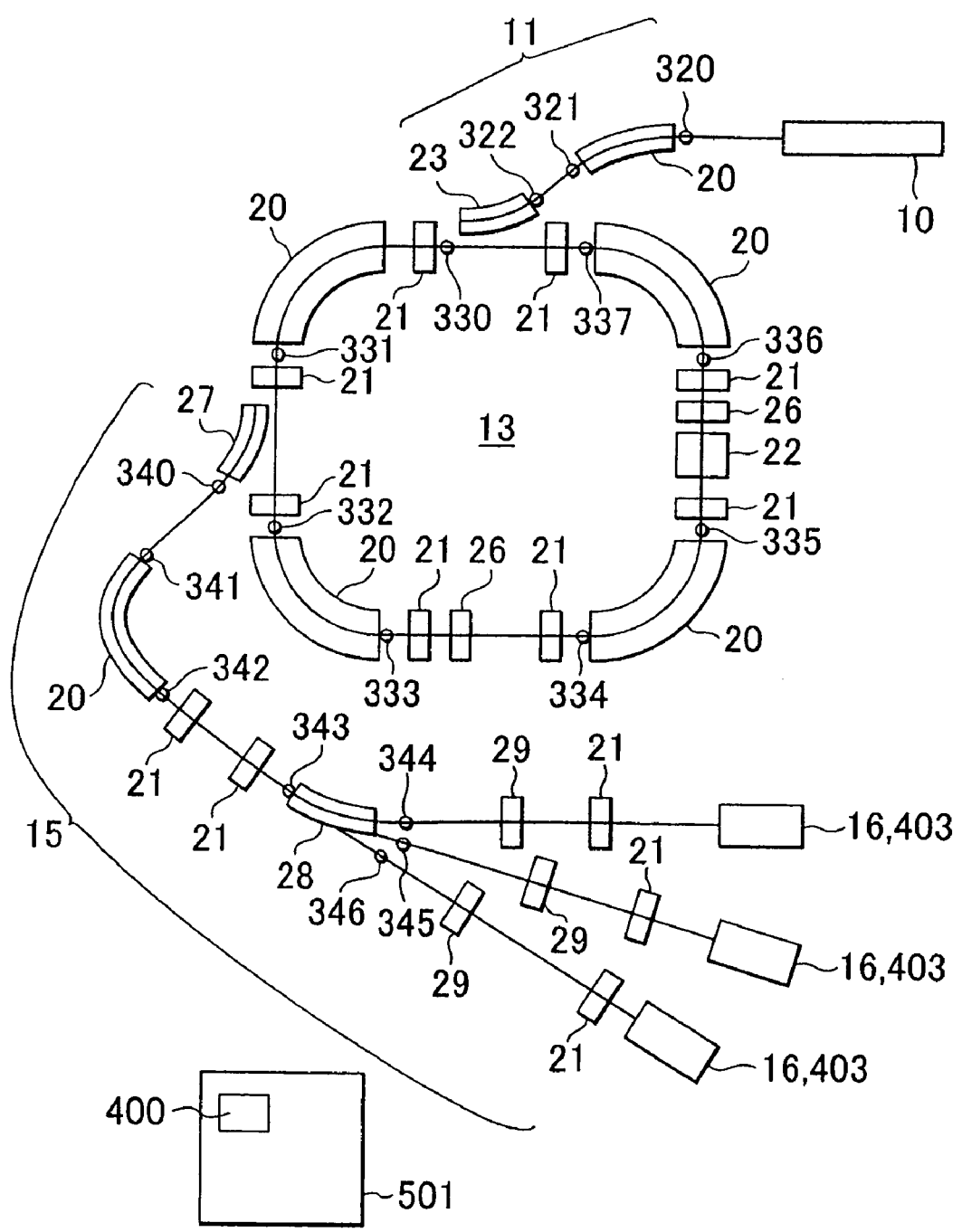
FIG. 1 is an overall constructional view of an embodiment according to the present invention.

Embodiments according to the present invention will be described with reference to the drawings. The medical accelerator control system according to this embodiment comprises a main body of an accelerator for performing the generation, acceleration, and accumulation of charged particle beams; irradiation rooms 16 in each of which an irradiation therapy is performed using charged particle beams extracted from the main body of the accelerator; irradiation operation rooms 403 for each outputting an irradiation start command; a controller 400 mainly performing control of a plurality of constituent components of the main body of the accelerator; and an accelerator control room 501 including the controller 400 principally and some user interface for setting and adjusting the accelerator. The accelerator control room 501 is disposed in a reasonable position within the facilities. The main body of the accelerator includes a pre-stage accelerator 10 for generating charged particle beams; a low-energy beam transport system (or simply referred to as a beam transport system; the same shall apply hereinafter) 11 for transporting the charged particle beams generated by the pre-stage accelerator 10 to a synchrotron for acceleration 13; the synchrotron for acceleration (i.e., accelerator) 13 for performing the acceleration and accumulation of charged particle beams and their extraction to each of the irradiation rooms 16; and a high-energy beam transport system 15 for transporting the charged particle beams extracted by the synchrotron for acceleration (i.e., accelerator) 13 to each of the plurality of irradiation rooms 16. The beam transport system 11 comprises a bending magnet 20 for bending charged particle beams, an injector 23 for injecting charged particle beams into the synchrotron 13 for acceleration, and current monitors 320 to 322 each measuring the beam current of charged particle beams.

The synchrotron 13 for acceleration includes bending magnets 20, quadrupole magnets 21 for performing the convergence and divergence of charged particle beams, steering magnets 26 for fine-tuning the position of charged particle beams, and an accelerating cavity 22 for accelerating charged particle beams, and current monitors 330 to 337.

The beam transport system 15 includes an extractor 27 for extracting charged particle beams from the synchrotron 13 for acceleration, a bending magnet 20 for bending charged particle beams, a switching magnet 28, dampers 29 each changing the beam current of charged particle beams, quadrupole magnets 21 for performing the convergence and divergence of charged particle beams, current monitors 340 to 346 each measuring the beam currents of charged particle beams, and irradiation rooms.

Figure 2:
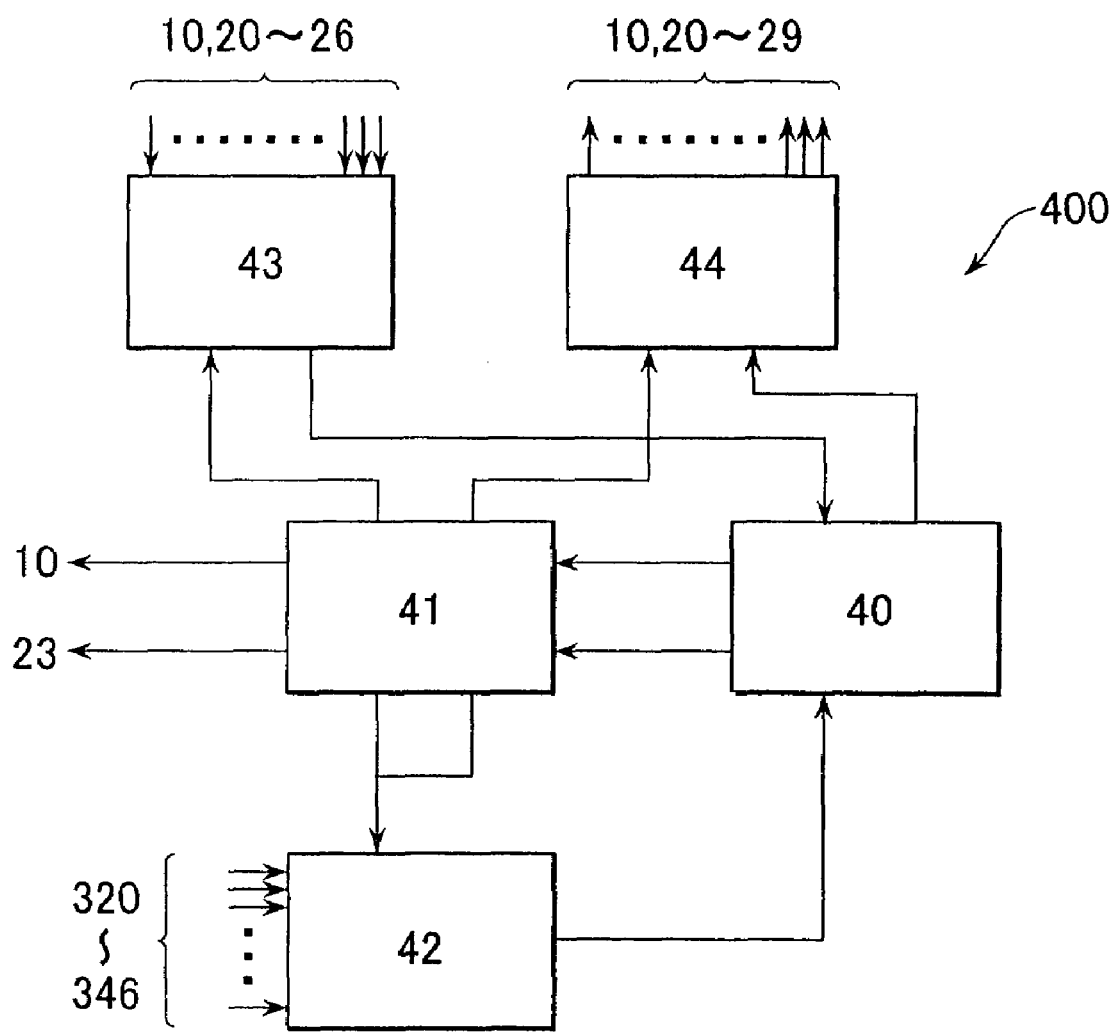
FIG. 2 is a diagram showing the details of the accelerator control.

FIG. 2 shows the controller 400 monitoring operations of the accelerator and performing the control of the accelerator. The controller 400 comprises a beam current measuring device 42 that measures the beam current of the accelerator at a predetermined timing; a control quantity measuring device 43 that measures, at predetermined timings, control quantities such as the cathode temperature of the pre-stage accelerator 10, the exciting currents of the bending magnets 20, quadrupole magnets 21, and steering magnets 26; a control quantity setting device 44 that sets the control quantities of the constituent components of the accelerator at predetermined timings; a trigger generation device 41 that generates trigger signals used for the measurement of the beam current by the beam current measuring device 42, the measurement of the control quantities by the control quantity measuring device 43, the setting of the control quantities by the control quantity setting device 44, and trigger signals used for the injection, extraction, acceleration, deceleration of charged particle beams in the accelerator (hereinafter, these trigger signals are referred to as various trigger signals); and a main controller 40 that determines the control quantities and the control timings of all constituent components.

Next, descriptions of the irradiation rooms and irradiation operation rooms will be provided.

Figure 3:
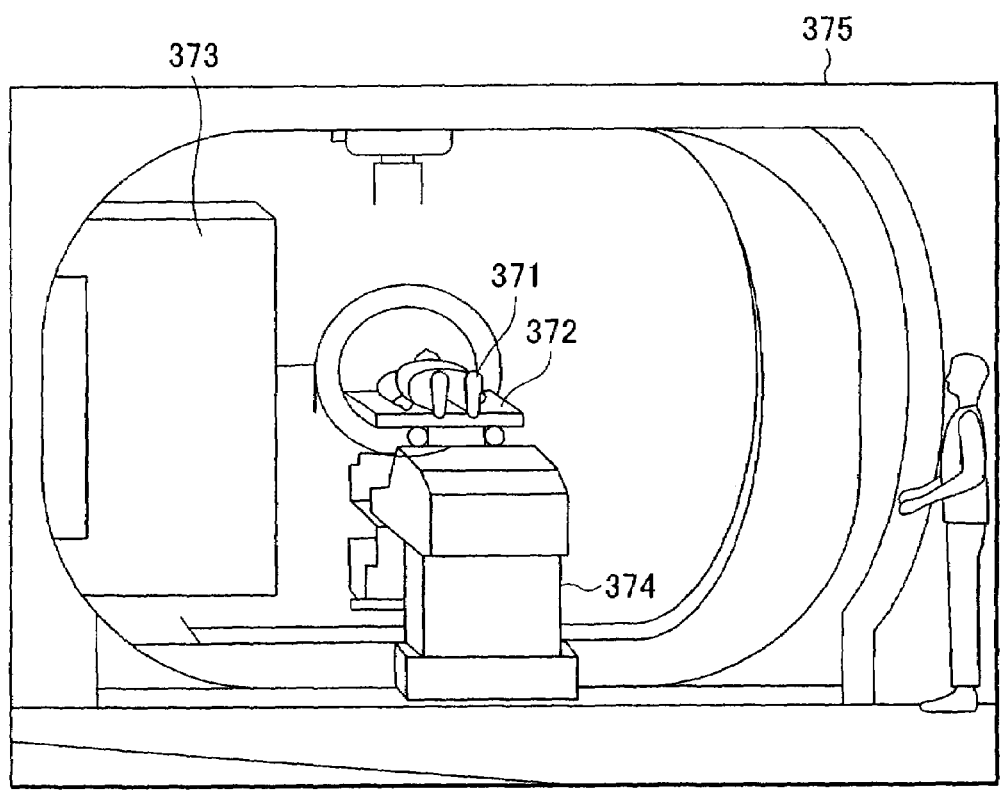
FIG. 3 is a perspective view showing the details of an irradiation room.

FIG. 3 shows an irradiation room 16. Irradiation rooms 16a to 16c are all set to be substantially the same. In the irradiation room 16, a patient 371 is laid on a couch 372.

The couch 372 is fixed to a couch stand 374. Proton beams accelerated by the accelerator (specifically, e.g., a synchrotron for acceleration is used) 13 are introduced to a proton beam irradiation nozzle 373 through the transport system, and applied to the patient 371. The proton beam irradiation nozzle 373 is fixed to a gantry 375. The gantry 375 is freely rotatable 360 degrees. With the rotation of the gantry 375, the proton beam irradiation nozzle 373 rotates relative to the couch 372.

Figure 4:
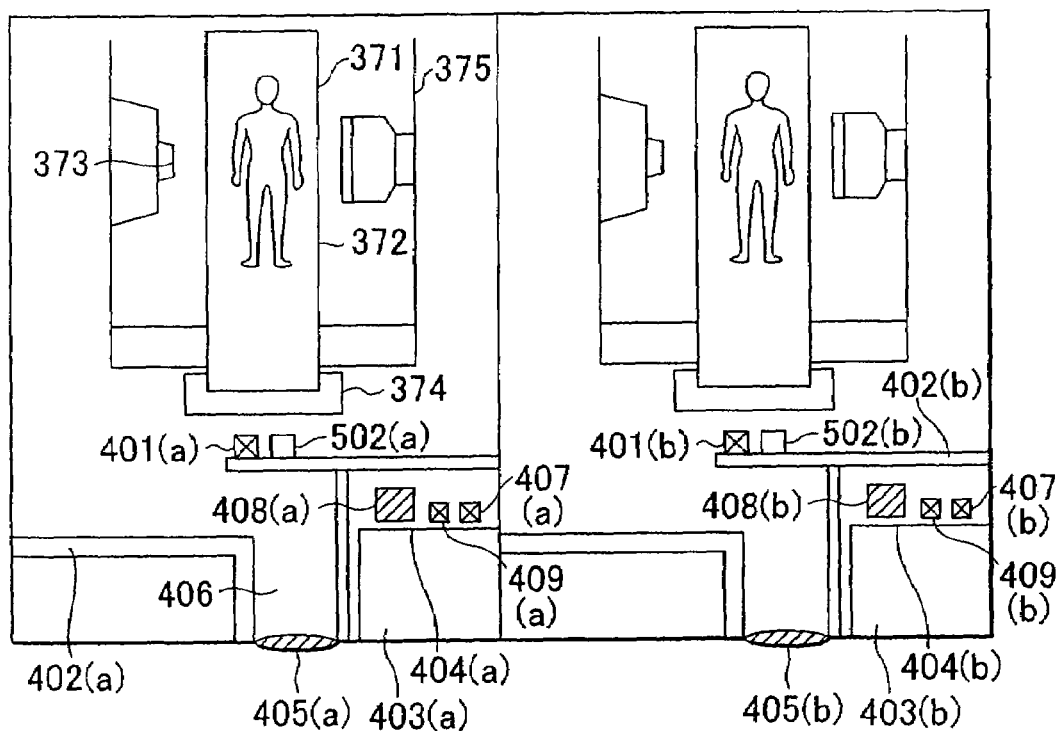
FIG. 4 is a diagram showing the positional relation between the irradiation rooms and the irradiation operation rooms.

FIG. 4 shows the details of the irradiation rooms 16. The irradiation rooms 16 each comprise a hard switch 401 for sending a beam request to the accelerator control room 501; an acceptance confirmation lamp 502; the gantry 375 irradiating the affected area of a patient from arbitrary directions; the couch 372 for fixing the patient; a labyrinth-like passage (wall) 406 and protective door 405 for blocking radiation. An irradiation operation room 403 is provided to each of the irradiation rooms 16 so that a shield wall 402 is interposed between them. The irradiation operation rooms 403 each have an operation console 404 equipped with a hard switch 407 for beam irradiation command, and a display device 408. In addition, the irradiation operation rooms 403 each have a hard switch 409 for beam request, in order that a beam request can be made even from each of the irradiation operation rooms 403.

The operator fixes the patient 371 to the irradiation position, and when an irradiation preparation has been completed, the operator depresses the hard switch 401 for beam irradiation request of the accelerator control room 501. Upon acceptance of this beam irradiation request, the acceptance confirmation lamp 502 blinks. At this time, in the accelerator control room 501, a startup of the accelerator for extracting required beam begins. Thereafter, the operator moves to the pertinent irradiation operation room 403 through a labyrinth-like passage 406 of the pertinent irradiation room 16. Upon completion of a beam irradiation preparation, a notification of the completion of the beam irradiation preparation is provided from the accelerator control room 501 to the irradiation room 16 and the irradiation operation room 403, and the acceptance confirmation lamp 502 and the display device 408 blink. The operator in the irradiation operation room 403 makes sure that beam is correctly set, by the display device placed on the operation console 404, and depresses the hard switch 407 for beam irradiation command that is disposed on the operation console 404, thereby making a request for a beam irradiation command.

Figure 5:
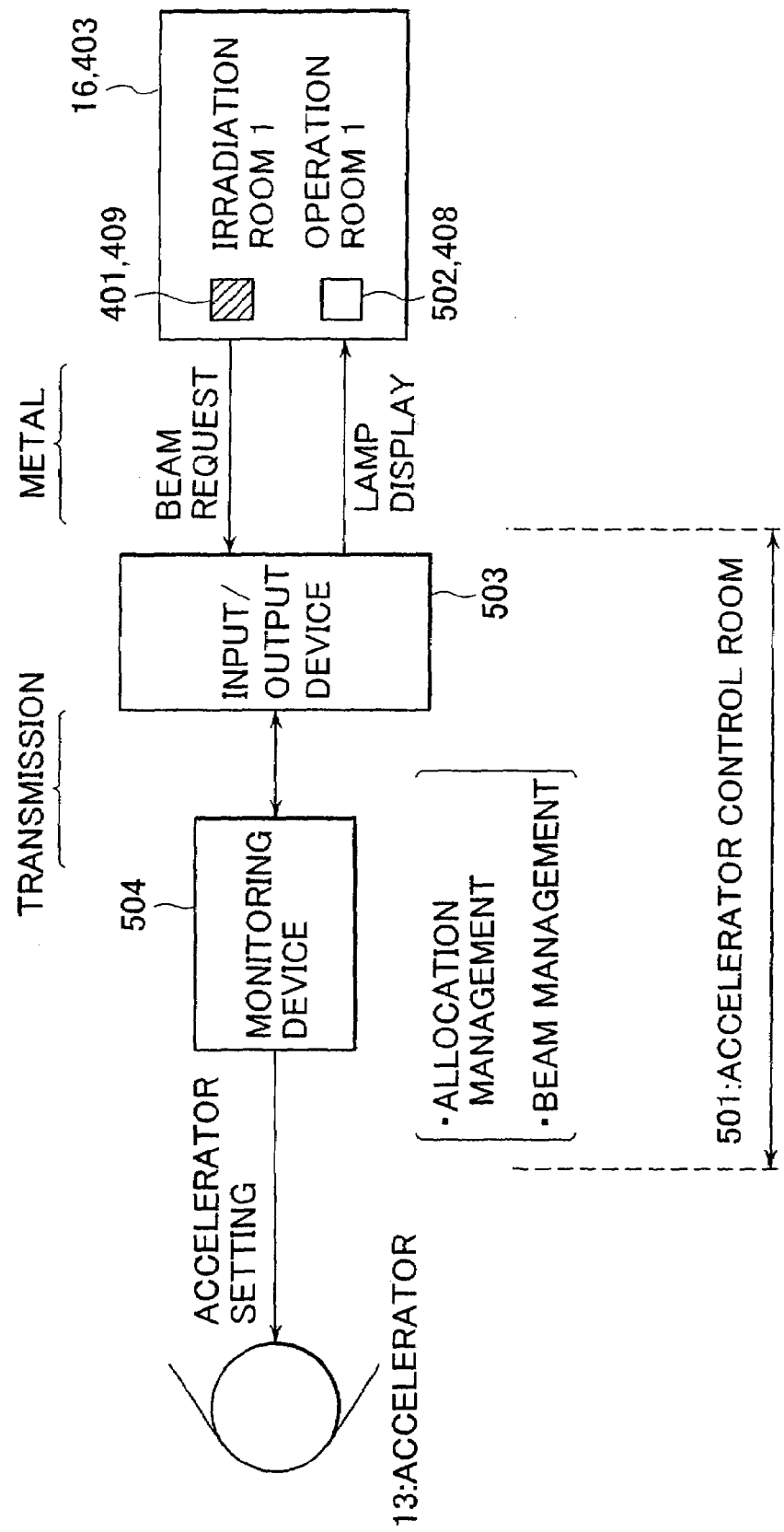
FIG. 5 is a diagram showing flows of signals from an operation room to the accelerator.

FIG. 5 shows an embodiment in which a single irradiation room 16 is provided with a hard switch 401 for beam irradiation request and a lamp 502. As shown in FIG. 5, upon depressing the hard switch 401 in the irradiation room, a beam irradiation preparation command is transmitted to the accelerator control room 501 by a metal signal. The acceptance of this request can be recognized by the acceptance confirmation lamp 502 entering a blinking state. Upon acceptance of the request from the irradiation room 16 through an input/output device 503, the accelerator 13 side retrieves, from database, the operation pattern that has been determined in advance in accordance with a beam irradiation request signal, and uniquely determines an automatic operation setting file for the accelerator 13. A monitoring device 504 determines which irradiation room 16 is to be allocated for beams from the accelerator 13, and monitors the setting states in the accelerator 13 and those between the accelerator 13 and the irradiation room 16. Here, the input/output device 503 and the monitoring device 504 are portions of components constituting the above-described controller 400. Upon completion of the beam irradiation preparation, a signal for beam request acceptance completion that indicates the preparation completion of the accelerator 13 is transmitted, by a metal signal, to the irradiation room 16 through the input/output device 503, and the acceptance confirmation lamp 502 in the irradiation room 16 is lighted. The signal for beam request acceptance completion is also transmitted to the irradiation operation room 403, and displayed on the display device 408. The operator in the irradiation room 16 makes sure by the display that equipment is correctly set, and make a request for a beam irradiation command.

Figure 6:
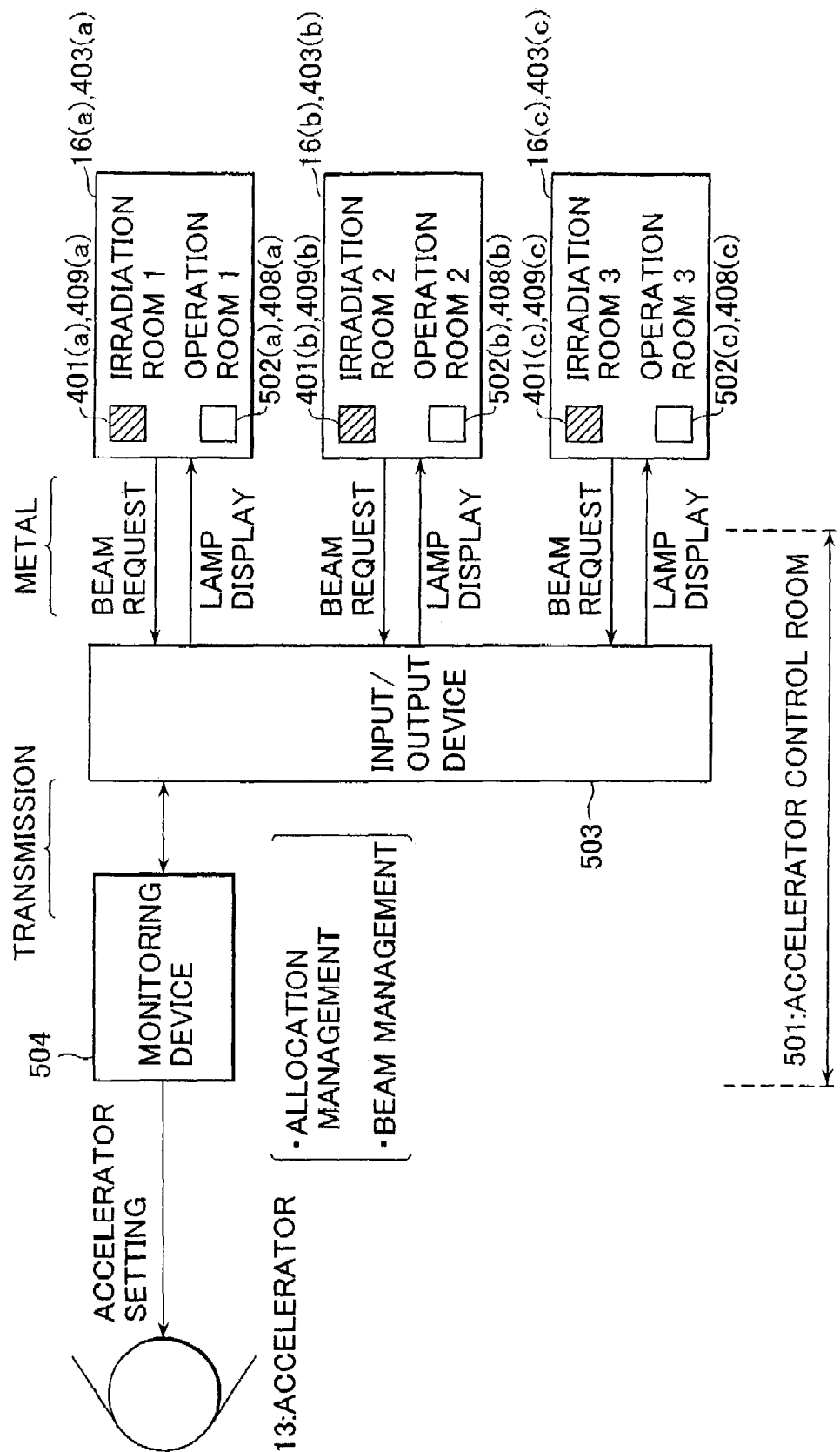
FIG. 6 is a diagram showing flows of signals from operation rooms to the accelerator.

FIG. 6 shows an embodiment in which a plurality of (three) irradiation rooms 16a to 16c, respectively, are provided with hard switches 401a to 401c for beam irradiation request, and lamps 502a to 502c. The basic operations in these three irradiation rooms are the same as those in a single irradiation room 16, but because a plurality of irradiation beam requests occur, priority processing must be performed with respect to them. The beam request acceptance on the accelerator 13 side is assumed to be performed in the order of the arrival of beam request. When the accelerator 13 side receives substantially simultaneously receives beam irradiation preparation requests from two or more of the operation rooms 16, the accelerator 13 side is assumed to accept a beam irradiation preparation request signal in accordance with a priority that has been determined in advance with respect to each of the operation rooms 16. After the accelerator 13 side has made the acceptance, a signal for beam request confirmation is transmitted, by a metal signal, from the accelerator control operation room 501 to each of the plurality of irradiation rooms 16 that have made the beam requests, through the input/output device 503, and the display of the lamp 502 in each of the pertinent irradiation rooms 16 becomes a blinking display. One possible method for notifying which room has been given a higher priority over the other is to change the lamp color, and this method may also be adopted as one embodiment of the present invention. The same signal as the foregoing is also sent to the display device 408 in each of the corresponding irradiation operation rooms 403, and the display device 408 likewise blinks.

Figure 7:
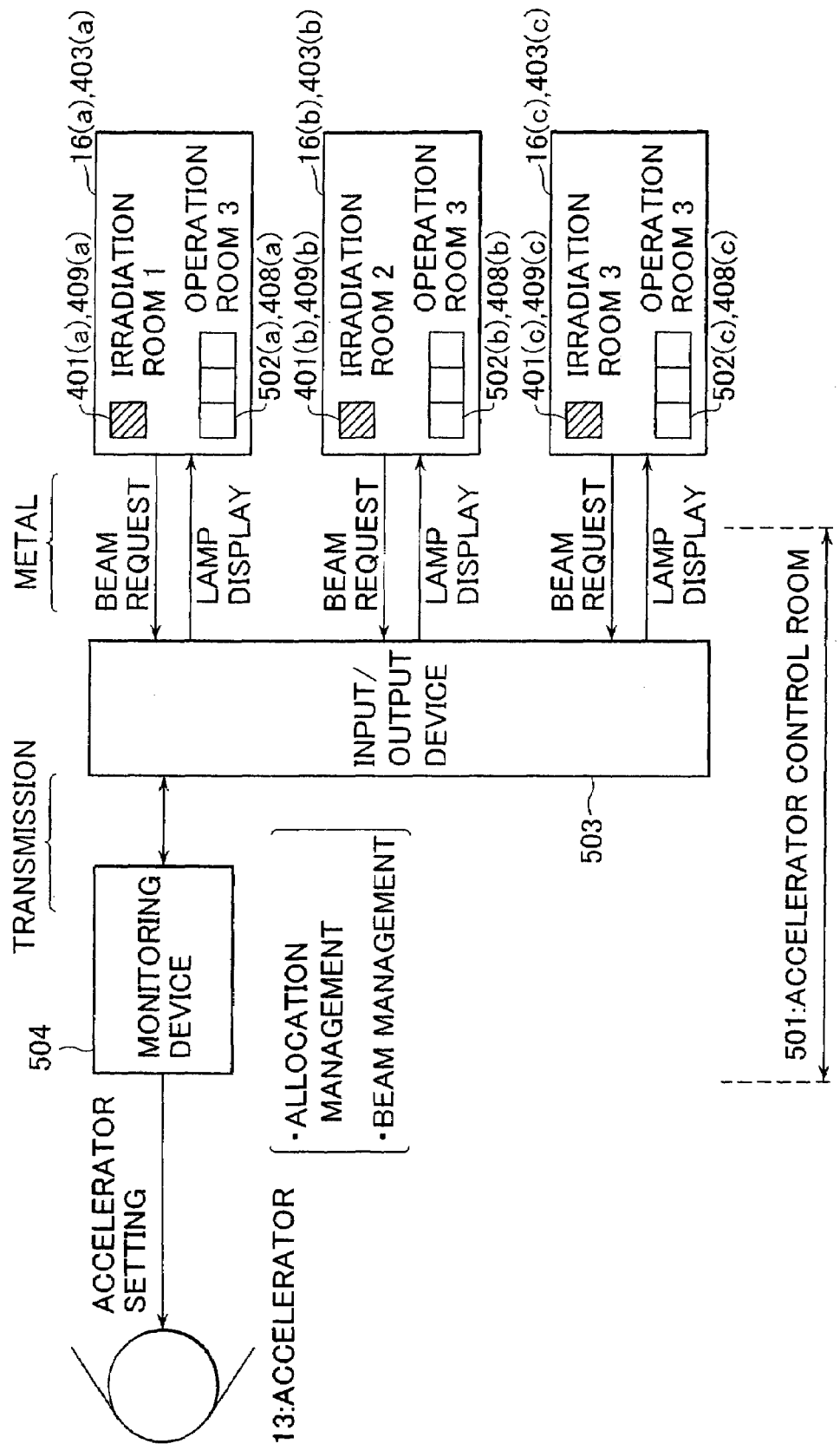
FIG. 7 is a diagram showing flows of signals from an operation room to the accelerator.
Figure 8:
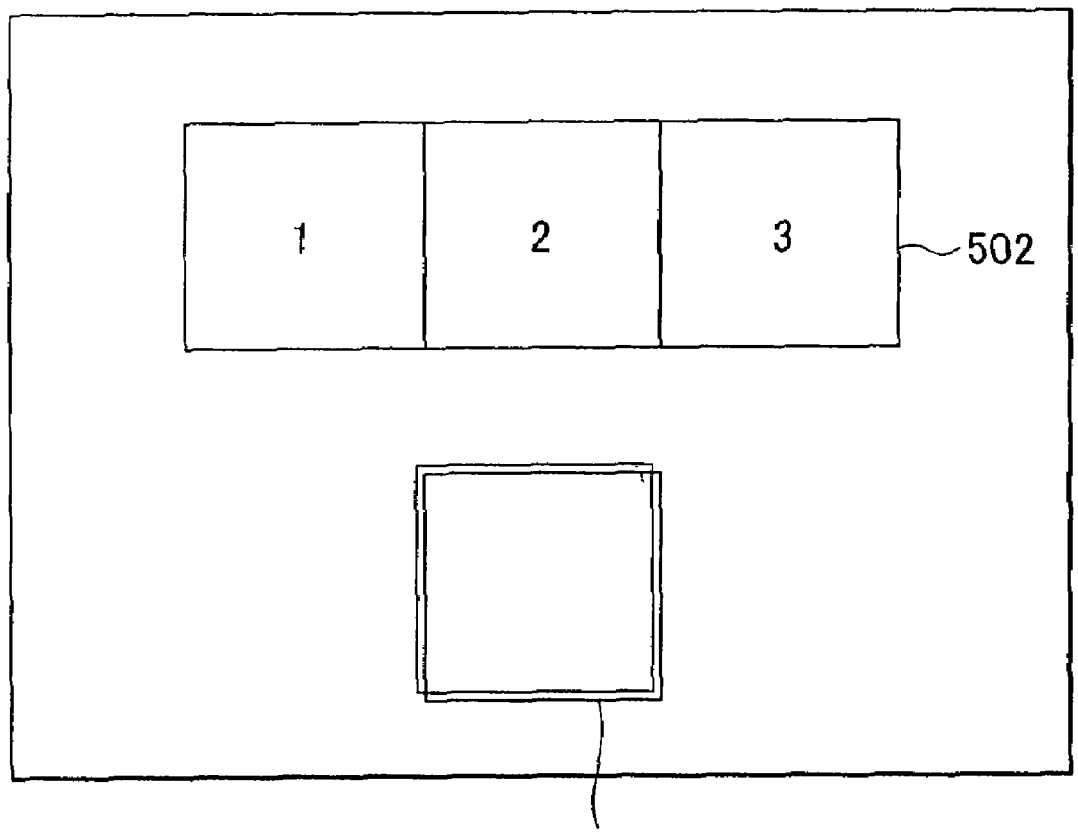
FIG. 8 is a diagram showing a hard switch for beam request, and lamps.

FIG. 7 shows an embodiment in which the plurality of (three) irradiation rooms 16a to 16c are provided with respective hard switches for beam irradiation request, and respective lamps displaying the irradiation request states of the respective irradiation rooms. As shown in FIG. 8, three lamps 502-1, 502-2 and 502-3 that are marked with the respective irradiation room numbers are provided in the vicinity of the respective hard switches 401 for beam irradiation request. The same displays as those in the three irradiation rooms 16 are also performed on the display devices 408 provided in the respective irradiation operation rooms 403, and thereby an operator in each of the irradiation rooms can check which irradiation room 16 is allocated for the accelerator, and can ascertain the reservation status and the order of irradiation. The operation regarding the irradiation beam request from a single irradiation room 16 is as described above, and in addition to this operation, a signal indicating the accelerator allocated state of an irradiation room 16 of which irradiation beam request has been accepted, is transmitted from the accelerator control room 501 to the pertinent lamp 502 in each of the irradiation rooms 16 through the input/output device 503. At this time, in each of the irradiation rooms 16, the display of the lamp 502 representing the irradiation room 16 of which the irradiation beam request has been accepted, becomes a lighting display indicating the accelerator allocated state. When irradiation beam requests are made from two or more of the irradiation rooms, a signal indicating the reservation state is transmitted, by a metal signal, from the accelerator 13 side to each of the irradiation rooms through the input/output device 503, with respect to irradiation beam requests other than the accepted irradiation beam request. At this time, in each of the irradiation rooms 16, the display of the lamp 502 representing the pertinent irradiation room 16 that indicates the reservation state becomes a blinking display indicating the reservation state. In this manner, regarding the display of the lamps 502, by changing the lamp display in a manner such as blinking, lighting, and lighting-out in correspondence with the reservation (accepted) state, allocated (ready) state, and non-reservation state, respectively, as described above, the operator can visually ascertain the state of each of the irradiation rooms 16 with ease. Upon completion of the irradiation in an irradiation room, an irradiation completion signal is automatically transmitted from the accelerator control side to each of the irradiation rooms 16, and the corresponding lamp in each of the irradiation room 16 is lighted out. Thereafter, an irradiation beam request acceptance signal that indicates the acceptance of an irradiation room 16 in a reservation waiting state, is transmitted from the accelerator 13 side to each of the irradiation rooms 16, and the display of the pertinent lamp becomes a lighting display in each of the irradiation rooms 16. The display of the display device 408 in the irradiation operation 403 is controlled in the same manner as the lamp 502 in the irradiation room 15.

As described above, according to the present invention, it is possible to reduce the accelerator allocated time, and improve the usage efficiency of the facilities by enhancing the throughput with respect to patients.

What is claimed is:

1. A charged particle therapy apparatus comprising:
a plurality of irradiation nozzles fixed to a plurality of irradiation rooms respectively and to which accelerated charged particle beams are introduced, a plurality of irradiation operation rooms, and a plurality of passages for allowing a person to move from the irradiation operation rooms to the irradiation rooms,
wherein said apparatus further comprises:
a first switch provided in each of said plurality of irradiation rooms for issuing an irradiation preparation request command requiring an irradiation preparation for charged particle beams; and
a second switch provided in each of the irradiation operation rooms for issuing a beam irradiation command requiring irradiation of charged particle beams; and
wherein said apparatus is configured such that when said beam irradiation command is issued from said second switch after said irradiation preparation request command has been issued from said first switch, charged particle beams are introduced to the corresponding irradiation nozzle.

2. The charged particle therapy apparatus according to claim 1, further comprising accelerator control means for uniquely determining an automatic operation setting file for an accelerator based on the beam request command.

3. The charged particle therapy apparatus according to claim 1, wherein the charged particle is a proton.

4. A charged particle therapy system comprising:
a beam generator for generating charged particle beams;
an accelerator for accelerating the charged particle beams; and
a plurality of irradiation nozzles fixed to a plurality of irradiation rooms respectively and to which the accelerated charged particle beams are introduced,
a plurality of irradiation operation rooms provided correspondingly to said plurality of irradiation rooms, and
a plurality of passages for allowing a person to move from the irradiation operation rooms to the corresponding irradiation rooms,
wherein said apparatus further comprises:
a first switch provided in each of said plurality of irradiation rooms for issuing an irradiation preparation request command requiring an irradiation preparation for charged particle beams; and
a second switch provided in each of the plurality of irradiation operation rooms for issuing a beam irradiation command requiring irradiation of charged particle beams; and
wherein said system is configured such that when said beam irradiation command is issued from said second switch after said irradiation preparation request command has been issued from said first switch, charged particle beams are introduced to the corresponding irradiation nozzle.

5. A charged particle therapy apparatus comprising:
a plurality of irradiation rooms in each of which a therapy is performed by irradiating a person to be treated with accelerated charged particle beams,
wherein said apparatus is configured such that when a beam irradiation command requiring irradiation is issued after a beam request command requiring an irradiation preparation for charged particle beams has been issued, charged particle beams are applied to the person to be treated; and
wherein said apparatus comprises a plurality of irradiation operation rooms provided to said plurality of irradiation rooms, and each of said plurality of irradiation rooms includes a passage for allowing an operator to move to the corresponding one of said plurality of irradiation operation rooms, and a switch for the beam request command is disposed in each of said plurality of irradiation rooms and a switch for the beam irradiation command is disposed in each of said plurality of irradiation operation rooms.

6. The charged particle therapy apparatus according to claim 5, further comprising accelerator control means for uniquely determining an automatic operation setting file for an accelerator based on the beam request command.

7. The charged particle therapy apparatus according to any one of claims 5 or 6, wherein the charged particle is a proton.

8. A charged particle therapy system comprising:
a beam generator for generating charged particle beams;
an accelerator for accelerating the charged particle beams; and
a plurality of irradiation rooms in each of which a therapy is performed by irradiating a person to be treated with the accelerated charged particle beams,
wherein said system is configured such that when a beam irradiation command requiring irradiation is issued after a beam request command requiring an irradiation preparation for charged particle beams has been issued, charged particle beams are applied to the person to be treated; and wherein said apparatus comprises a plurality of irradiation operation rooms provided to said plurality of irradiation rooms, and each of said plurality of irradiation rooms includes a passage for allowing an operator to move to the corresponding one of said plurality of irradiation operation rooms, and a switch for the beam request command is disposed in each of said plurality of irradiation rooms and a switch for the beam irradiation command is disposed in each of said plurality of irradiation operation rooms.

* * * * *